United States Patent [19] [11] 4,203,975
Greven [45] May 20, 1980

[54] PSYCHOPHARMACOLOGICAL PEPTIDES SUITABLE FOR THERAPEUTIC ADMINISTRATION

[75] Inventor: Hendrik M. Greven, Heesch, Netherlands

[73] Assignee: Akzona Incorporated, Asheville, N.C.

[21] Appl. No.: 921,067

[22] Filed: Jun. 30, 1978

[30] Foreign Application Priority Data

Jul. 13, 1977 [NL] Netherlands ............... 7707781

[51] Int. Cl.² ............... A61K 37/00; C07C 103/52
[52] U.S. Cl. .................. 424/177; 260/112.5 R
[58] Field of Search ............ 260/112.5 R; 424/177

[56] References Cited

U.S. PATENT DOCUMENTS 3,803,119  4/1974  Tamura et al. ............ 260/112.5 R
3,835,110  9/1974  Greven et al. ............ 260/112.5 R

OTHER PUBLICATIONS

M. E. Celis et al., Chem. Abstr. 85 (1976), 154229y.
Jenkins et al., The Chemistry of Organic Medicinal Products, p. 457.

Primary Examiner—Delbert R. Phillips
Attorney, Agent, or Firm—Robert H. Falk; Charles A. Wendel; Francis W. Young

[57] ABSTRACT

Novel peptides of the formula

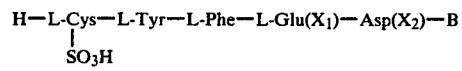

are disclosed (together with pharmaceutical compositions comprising a pharmaceutically effective amount of same) wherein $X_1$ and $X_2$ represent an hydroxy or amino group and B represents:
(1) hydroxy or
(2) an amino-acid residue selected from the group consisting of L-Asp-OH, L-Asn-OH, L-Glu-OH, L-Gln-OH, L-Ser-OH, or HN-A-COOH, wherein A is an alkylidene group from 1 to 6 carbon atoms;

or a functional derivative thereof.

These peptides have psychopharmacological properties; they are suitable for the treatment of certain mental disorders in which stimulation of brain function is desired, such as for the treatment of senility or amnesia.

18 Claims, No Drawings

PSYCHOPHARMACOLOGICAL PEPTIDES SUITABLE FOR THERAPEUTIC ADMINISTRATION

BACKGROUND OF THE INVENTION

1. Field of the Invention

The invention described and claimed herein relates to psychopharmacologically active peptides, methods of preparing such compounds, and pharmaceutical compositions in a form suitable for therapeutic administration containing these peptides, and to those peptides suitable for the treatment of mental disorders, in which a stimulation of brain function is desired, e.g. for the treatment of senility and/or amnesia.

2. Description of Prior Art and Other Information

It is known from 157 NEUROPHARMACOL 4 (1965) that the nonapeptide derivative (Lys)-vasopressin zinc tannate possesses certain psychopharmacological properties when administered to rats, from which the hypophysis or the posterior lobe thereof has been removed. Specifically, this nonapeptide was alleged to be capable of inhibiting the extinction of the conditioned flight response. It is known that the extremely powerful pressor activity of vasopressin and its functional derivatives constitutes, however, a very unpleasant side-effect.

It is furthermore known to those in the art from U.S. Pat. No. 3,835,110 that a pentapeptide with the formula

H-L-Cys-L-Tyr-L-Phe-L-Glu(X)-L-Asp(X)-OH or the dimer formed from this via a disulphide (S-S) bridge, inhibits the extinction of the conditioned avoidance response to at least the same extent as the nonapeptides above (specifically when on subcutaneous administration), but displays no pressor activity whatsoever. An objection to most peptides of this group is, however the extraordinarily poor solubility in most solvents, as a result of which purification, the usual performing of analyses and the pharmaceutical processing of these peptides is an extremely difficult and tiresome task.

Vasopressin polypeptide derivatives are furthermore prepared and shown in U.S. Pat. Nos. 3,299,036; 3,422,083 and 3,743,726. The compounds disclosed in U.S. Pat. No. 3,299,036 are particularly useful in the prophylaxis and therapy of parenchymatous bleeding. Further, the polypeptides of U.S. Pat. No. 3,422,083 have at least one α (-methylidene) group replaced by a nitrogen atom, and the compounds of U.S. Pat. No. 3,743,726 are octapeptides that stimulate the acquisition of the conditional avoidance response and inhibit its extinction. Representative patents directed to sulfonated/sulfated peptides are U.S. Pat. Nos. 3,579,494 and 3,705,140.

SUMMARY OF THE INVENTION

Novel peptides have now been found of the formula:

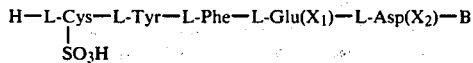

H—L-Cys—L-Tyr—L-Phe—L-Glu(X₁)—L-Asp(X₂)—B
|
SO₃H wherein $X_1$ and $X_2$ represent an hydroxy or amino group and B represents:

(1) hydroxy or (2) an amino acid residue selected from the group consisting of L-Asp-OH, L-Asn-OH, L-Glu-OH, L-Gln-OH, L-Ser-OH, or HN-A-COOH, wherein A is an alkylidene group from 1 to 6 carbon atoms, or a suitable functional derivative thereof. These novel peptides inhibit the extinction of the conditioned avoidance response in rats. They are furthermore active in the amnesia test in rats, from which appears that the present peptides can reverse and/or prevent memory loss. The peptides of this new class are better soluble in most solvents than those described in U.S. Pat. No. 3,835,110. Especially preferred are the peptides (and compositions containing an effective amount of same) in which B represents the amino acid residue L-Asp-OH; these peptides have been found to be especially suitable for oral administration, having distinctly better oral activity. By "alkylidene group" in the definition A of formula I it is meant straight or branched-chain alkylidene hydrocarbons, otherwise unsubstituted.

DESCRIPTION OF THE PREFERRED EMBODIMENTS

The peptides according to the general formula I are prepared in steps each of which are known to those in the art. The methods which are most frequently used for the preparation of the compounds herein referred to may be summarized as follows in three alternative processes:

(a) condensation in the presence of a condensing agent of (1) an amino acid or peptide containing a free carboxyl group (and in which other reactive groups have been protected) with (2) a compound (amino acid, peptide) containing a free amino group (and in which other reactive groups have likewise been protected); or (b) condensation of an amino acid or peptide containing an activated carboxyl group, and in which other reactive groups have optionally been protected, with (2) a compound (amino acid, peptide) containing a free NH₂ group (and in which other reactive groups have been protected), or (c) condensation of an amino acid or peptide containing a free carboxyl group (and in which other reactive groups have been protected) with (2) a compound (amino acid, peptide) containing an activated amino group (and in which other reactive groups have optionally been protected);

after which an S-protecting group, if present, and optionally the other protecting groups are removed and, if necessary, the S-sulpho group is introduced. Protecting groups which are still present are then removed.

Methods of activating the carboxyl group are known to those skilled in the art, and include conversion of same into an acid halide, an azide, anhydride, imidazolide, or an activated ester such as the N-hydroxysuccinimide ester or the p-nitrophenyl ester.

The amino group may be activated by known methods to those in the art, including converting the amino group into a phosphite amide, or by using the "phosphor-azo" method. See for both methods of activating: Houben-Weyl, Methoden der Organischen Chemie, 4th edition, Volume XV/2 (Georg Thieme Verlag, Stuttgart 1974), incorporated herein by reference.

The most usual methods for the above-noted condensation reactions are: the carbodi-imide method, the azide method, the mixed anhydride method, and the activated ester method, as described in E. Schröder and K. Lubke, "The Peptides", volume I, 1965 (Academic Press), incorporated herein by reference. The so-called "solid phase" method of Merrifield, described in 85 J. AMER.CHEM.SOC. 2149 (1963), also incorporated herein by reference, may furthermore also be used for the preparation of the peptides and peptide derivatives herein described.

The reactive groups which are not to participate in the condensation reaction are effectively protected by suitable so-called "protecting groups" which in turn are later readily removed by hydrolysis or reduction. A carboxyl group may, for example, be effectively protected by esterification with at least a stochiometrically effective amount of methanol, ethanol, tertiary butanol, benzyl alcohol or p-nitrobenzyl alcohol, or in the alternative, by conversion by known means into an amide, as, for example, described in Houben Weyl; Methoden der Organischen Chemie, 4th edition, Volume XV/1, page 315 seq. This last protecting group is however very difficult to remove, so that it is recommendable that this group only be used to protect the carboxyl group of the C-terminal amino-acid in the final peptide. In this case, the peptides synthesis leads directly to the amide of the peptide according to the general formula I.

Groups which may effectively protect an amino group are generally suitable acid groups, for example, an acid group derived from suitable aliphatic, aromatic, araliphatic or heterocyclic carboxylic acids (such as acetic acid, benzoic acid, pyridinecarboxylic acid), or an acid group derived from carbonic acid (such as ethoxy-carbonyl, benzyloxy-carbonyl, t-butyloxy-carbonyl or p-methoxybenzyloxy-carbonyl), or an acid group derived from a sulphonic acid (such as benzenesulphonyl or p-toluene-sulphonyl). Other groups may also be used, such as substituted or unsubstituted aryl- or aralkyl-groups, for example benzyl and triphenylmethyl, or groups such as o-nitrophenylsulphenyl or 2-benzoyl-1-methylvinyl. (See Houben Weyl, Methoden der Organischen Chemie, 4th edition, Volume XV/1, page 46 seq.).

The mercapto group of cysteine may, for example, be effectively protected by acylation or (ar)-alkylation. Suitable acyl groups are acetyl or benzoyl; usual (ar)alkyl groups are tert. butyl, benzyl, p-NO$_2$-benzyl, trityl or acetamidomethyl. (See Houben-Weyl; already referred to, Volume XV/1, page 736 seq.). Said mercapto group may, however, also be "protected" with the SO$_3$H group. Obviously, the latter group should be maintained after the peptide-synthesis. Although it is not absolutely essential, it is sometimes preferred and recommended that the hydroxyl group of tyrosine also be protected; this group is preferably protected by a tertiary butyl group.

The protecting groups may be removed by various conventional methods known to those in the art, depending on the nature of the protecting group concerned, for example by hydrolysis with the aid of trifluoro-acetic acid, hydrogen iodide or hydrogen bromide in glacial acetic acid, or by reduction, as with catalytic hydrogenation or sodium in liquid ammonia. (See the references, already referred to).

The deprotection of the mercapto group of cysteine leads in general to complete or partial dimerization of the peptide unless special measures are taken to avoid this, such as performing the deprotection reaction under a nitrogen atmosphere and use of reagents and solvents which are completely free from oxygen. Preventing a possible dimerization is however not immediately essential, since the sulphonation of the cysteinyl residue (still to be performed) can be performed with either the monomer or the dimer. It may even be advantageous to perform the essential introduction of the S-sulpho group exclusively in the dimer.

A complete dimerization of the S-deprotected peptide is obtained by oxidation of the mercapto groups of two monomeric peptide molecules to give a disulphide. This oxidation is brought about in a way which is usual and known to those in the art for such oxidations, for example by oxidation with potassium ferricyanide, iodine or ethyl iodide or by means of an oxidation with air or oxygen in water or liquid ammonia. When a suitable choice of protecting groups has been made, it is also possible to perform the oxidation on the still protected peptide, for example, by known means such as on treatment of an S-trityl protected peptide with iodine in a suitable solvent such as methanol, the trityl group is split off with simultaneous oxidation of the resultant —SH group to a disulphide. (See Houben Weyl: Volume XV/1, page 800 seq.).

The dimer as well as the S-sulpho containing peptide can also be prepared directly via the usual peptide syntheses. In stead of protected cysteine, use is made in these syntheses of the amino acids cystine and Cys(-SO$_3$H) respectively. This direct route has of course the advantage that no S-protecting group has to be introduced, nor does dimerization of the monomer occur.

Where the S-sulpho group is not present already, the last step in the preparation of the present peptides of general formula I consists of the introduction of the S-sulpho group in a peptide of the general formula:

or the corresponding dimer thereof with the formula:

or a functional derivative where B, X$_1$ and X$_2$ have the meaning given above and where the amino group of Cys, the OH-group of Tyr and/or the carboxyl group(s) are optionally provided with protecting groups.

The sulphonation or introduction of the S-sulpho group is preferably achieved with the aid of a suitable alkali metal sulphite or alkali metal hydrogen sulphite, in particular sodium sulphite (Na$_2$SO$_3$) or sodium hydrogen sulphite (NaHSO$_3$), in a suitable inert solvent, preferably water. The sulphonation is usually performed at room temperature or at a somewhat lower temperature (above about 0° C. to about 25° C.). The ratio peptide:sulphite in this sulphonation is preferably from about one equivalent peptide to about two equivalents sulphite.

If the dimer is sulphonated, or the monomer is sulphonated without complete exclusion of oxygen, then it is recommendable that an oxidising agent, such as an effective amount of Na$_2$S$_4$O$_6$, also be added to the reaction mixture. This oxidising agent helps to ensure that the non-sulphonated monomer is immediately converted into the dimer.

Under the term suitable functional derivatives of the peptides according to the general formula I are understood:

(a) salts, formed by reaction of the peptide with a base, preferably a base derived from an alkali metal, for example NaOH, Na$_2$CO$_3$ or NaHCO$_3$;

(b) esters, preferably derived from aliphatic alcohols with one to about eighteen carbon atoms, in particular from alkanols with one to about six atoms, such as methanol, ethanol, propanol, isopropanol, butanol, amylalcohol and iso-amyl alcohol;

(c) amides or alkyl-substituted amides, where the alkyl group(s) possess(es) 1–4 C-atoms; and (d) metal complexes, formed by bringing the peptides herein referred to into contact with a sparingly soluble salt, hydroxide or oxide of a metal, preferably zinc.

Salts may be obtained directly from the reaction milieu in which the peptides are prepared or they may be prepared later by the reaction of the peptide with a base. The sodium salts are preferred.

Esters of the peptides herein described may be obtained by esterifying the peptide-acid in the usual way. It is however preferable that the ester group be introduced during the peptide synthesis, namely by using the desired ester of the amino acid concerned as starting material instead of the amino acid itself. This last method is advantageous in that the ester group also functions as protecting group.

Amides may be prepared by aminolysis of a peptide ester. It is also preferable in this case that the desired amide group be present in the starting material. If, for example, the amide is required of a peptide according to formula I where B represents the amino acid residue -Ser-OH, then it is by far the most preferable that the amide of the amino acid serine be used as starting material instead of the amino acid itself.

The peptides, peptide derivatives, and compositions with a pharmaceutically effective carrier, herein referred to, possess valuable psychopharmacological properties. Specifically, they inhibit the extinction of conditioned avoidance behavior, and are active in the amnesia test, already described herein before, so that they are eminently suitable for the treatment of certain mental disorders in which stimulation of brain function is desired, such as senility or amnesia.

The peptides are used in effective amounts with known carriers, and preferably used in a dosage of 0.01 to 10 mg per kg body weight per day, depending on the form in which they are administered.

The peptides according to the invention may be administered by either the oral or the parenteral routes, by means of a pharmaceutically effective carrier known to those skilled in the art. For the purposes of injection they are dissolved, suspended or emulsified in a suitable liquid, sterilized and then filled into ampoules under aseptic conditions. Mixed with suitable excipients and fillers, the peptides herein referred to may further be provided in a form suitable for oral administration, such as pills, tablets, dragees or capsules. The peptides herein described may furthermore be administered in the form of a suppository or spray.

The form for oral administration is preferred.

Particularly valuable preparations are obtained when the peptides herein referred to are provided in a form conferring prolongation of activity. Preferably, the metal complexes are used. These metal complexes may be obtained by bringing the peptides into contact with sparingly soluble metal salts, metal hydroxides or oxides known to those in the art. The metal phosphates, metal pyrophosphates and metal polyphosphates are generally used as sparingly soluble metal salts.

Metals which may be used in this process are those metals belonging to the b-groups of the Periodic Table for example cobalt, nickel, copper, iron and preferably zinc, as well as metals from the main groups of the Periodic Table which are capable of forming complexes, such as magnesium and aluminium. The preparation of the said metal complexes takes place in the usual way.

The metal complexes may be obtained by adding the peptide and a sparingly soluble metal salt, metal hydroxide or metal oxide to an aqueous medium. The metal complex may also be obtained by adding an alkaline medium to an aqueous solution of the peptide and a soluble metal salt, as a result of which the insoluble peptide-metal hydroxide complex is formed.

The metal complex may furthermore be obtained by adding the peptide, a soluble metal salt and a soluble salt to an aqueous, preferably alkaline, medium, as a result of which the insoluble peptide-metal salt complex is formed in situ.

The metal complexes may be used directly as suspensions or they may for example be freeze-dried and at a later date resuspended by the usual methods known to those in the art.

Peptides according to the general formula I, and peptide derivatives thereof, which are preferred are those peptides in which B represents the amino acid residue L-Asp-OH. These latter peptides differ from the known, earlier named pentapeptides according to U.S. Pat. No. 3,835,110, not only through considerably improved solubility but above all through distinctly better oral activity. This improvement of the oral activity is not related to the increased solubility; the peptides according to general formula I in which B represents a hydroxy group, are also readily soluble but do not display a significant improvement of oral activity compared with the known pentapeptides of U.S. Pat. No. 3,835,110.

The following observations are made with respect to the examples and claims which follow:

I. If no optical configuration is stated, the L-form is meant.

II. The following abbreviations have been used for the protecting or activating groups:
Z = benzyloxycarbonyl
tBu = tertiary butyl
Me = methyl
Bzl = benzyl III. The following abbreviations have been assigned to the solvents and reagents used:
Bu = butanol
Py = pyridine
Ac = acetic acid
Wa = water
DMF = dimethylformamide
DCCI = dicyclohexylcarbodi-imide
DCCU = dicyclohexylurea
HOBT = N-hydroxybenztriazole IV. The following abbreviations have been used for the amino acid groups:
Cys = cysteinyl
Tyr = tyrosyl
Phe = phenylalanyl
Gln = glutaminyl; similar to Glu(NH$_2$)
Asn = asparaginyl; similar to Asp(NH$_2$)
Glu = glutamyl
Asp = aspartyl
Ser = seryl the group —HN—A—COOH includes i.a. the amino acid residues:

glycyl, alanyl, valyl, leucyl and isoleucyl; the amino acid residue

has the structural formula:

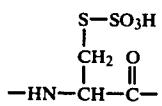

Although the invention has been described with respect to the specific embodiments above, numerous variations and modifications will become evident to those skilled in the art, without departing from the scope and spirit of the invention as described above, defined in the appended claims, and as shown in the following examples.

PREPARATION OF STARTING MATERIALS

A. Preparation of protected penta- and hexapeptides

1. Z-Cys(Bzl)-Tyr-Phe-Gln-Asn-OH (see U.S. Pat. No. 3,835,110)

0.26 ml N-ethylmorpholine is added to 1 g Z-Cys(Bzl)-Tyr-OH dissolved in 10 ml THF, and the solution is cooled to $-10°$ C., after which 0.26 ml isobutylchloroformate is added. After stirring for about 10 minutes at $-10°$ C., 0.8 g H-Phe-Gln-Asn-OH and 0.26 ml N-ethylmorpholine in about 10 ml cooled DMF are added. After stirring for 30 minutes at $-10°$ C., about 2 hours at $0°$ C. and about 18 hours at $20°$ C., the reaction mixture is poured into water and the pH is adjusted to 3–4. The solid substance formed is removed by centrifugation. The product thus obtained is crystallized from ethanol/water (1:1). Melting point 219° C. (decomposition); Rf in Bu:Py:Ac:Wa (4:0.75:0.25:1)=0.44 on SiO$_2$, Rf in Bu:Ac:Wa (4:1:1)=0.34 on SiO$_2$.

2. Z-Cys(Bzl)-Tyr-Phe-Gln-Asn-Asp-OH 4.54 g of the peptide obtained in 1. is dissolved in 400 ml DMF and the solution is cooled to $-5°$ C., after which 1.25 g H-Asp(OtBu)-OtBu, 0.81 g HOBT and 1.14 g DCCI are added consecutively. The mixture is then stirred for about 30 minutes at $-5°$ C., about one hour at $0°$ C. and for about 15 hours at room temperature.

The DCHU formed is filtered off and the filtrate is poured into 1500 ml ethyl acetate containing 30 ml ethanol. The crystals thus formed are filtered off and dried. Yield of t-butyl ester: 4.05 g; melting point 190° C. (decomposition). The t-butyl ester obtained is subsequently hydrolysed in a mixture of 40 ml 90% trifluoroacetic acid and 0.5 ml anisole at room temperature. After stirring for 30 minutes, the mixture is poured into 300 ml ether, after which the crystals obtained are filtered off and dried.

Yield (peptide acid): 3.5 g; melting point 224°–225° C.; Rf in Bu:Ac:Wa (4:1:1)=0.25 on SiO$_2$.

3. The following peptides are obtained in a way corresponding to that described in 2.:

(a) Z-Cys(Bzl)-Tyr-Phe-Gln-Asn-Glu-OH, Rf in Bu:Ac:Wa (4:1:1)=0.30 (SiO$_2$)

(b) Z-Cys(Bzl)-Tyr-Phe-Gln-Asn-Ser-OH, Rf in Bu:Ac:Wa (4:1:1)=0.10 (SiO$_2$)

(c) Z-Cys(Bzl)-Tyr-Phe-Gln-Asn-Ala-OH, Rf in Bu:Ac:Wa (4:1:1)=0.35 (SiO$_2$)

(d) Z-Cys(Bzl)-Tyr-Phe-Gln-Asn-Val-OH, Rf in Bu:Ac:Wa (4:1:1)=0.37 (SiO$_2$).

B. Preparation of dimers from protected penta- and hexapeptides

1.

(H—Cys—Tyr—Phe—Gln—Asn—OH)$_2$ 5.0 g of the protected pentapeptide obtained in A.1. is dissolved in about 1000 ml liquid ammonia. After stirring for 15 minutes, two equivalents NaNH$_2$ are then added to the solution.

Sodium is subsequently added to the solution until a blue color appears and lasts for about 30 seconds, after which the ammonia is allowed to evaporate into the air. The residue is added to about 500 ml water and an equimolar amount of HCl, with respect to Na and NaNH$_2$. The pH of the mixture is adjusted to 6.8, after which a trace of copper chloride is added to the mixture and air is passed through for 24 hours. A tertiary reaction for —SH groups is then negative. The reaction mixture is subsequently put on an acid ion-exchange column, after which the mixture is eluted with a 2% acetic acid solution until no more chloride ions can be demonstrated. The peptide is subsequently eluted from the column with a 50% solution of acetic acid. The eluate is then freeze-dried and suspended in water, whereby the pH is held at 4.1. The thus-obtained crystals are filtered off and dried. Melting point 240° C. (decomposition); Rf in Bu:Ac:Wa (4:1:5)=0.44 on SiO$_2$.

2. The following dimers are obtained in a way corresponding to that given in B.1.:

(a)

(H—Cys—Tyr—Phe—Gln—Asn—Asp—OH)$_2$;

melting point 230° C. (dec.); Rf in Bu:Ac:Wa (3:1:1)=0.10 (SiO$_2$)

(b)

(H—Cys—Tyr—Phe—Gln—Asn—Glu—OH)$_2$;

melting point 200° C. (dec.); Rf in Bu:Ac:Wa (3:1:1)=0.14 (SiO$_2$)

(c)

(H—Cys—Tyr—Phe—Gln—Asn—Ser—OH)$_2$;

melting point 180° C. (dec.); Rf in Bu:Ac:Wa (3:1:1)=0.07 (SiO$_2$)

(d)

(H—Cys—Tyr—Phe—Gln—Asn—Ala—OH)$_2$;

melting point 184° C. (dec.); Rf in Bu:Ac:Wa (3:1:1)=0.15 (SiO$_2$)

(e)

(H—Cys—Tyr—Phe—Gln—Asn—Val—OH)$_2$;

melting point 190° C. (dec.); Rf in Bu:Ac:Wa (3:1:1)=0.17 (SiO₂)

(f) (H—Cys—Tyr—Phe—Glu—Asp—OH)₂;

(g) (H—Cys—Tyr—Phe—Glu—Asn—OH)₂;

(h) (H—Cys—Tyr—Phe—Gln—Asp—OH)₂;

(j) (H—Cys—Tyr—Phe—Gln—Asn—OC₁₁H₂₃)₂.

The dimers (f), (g), (h) and (j) being disclosed already in U.S. Pat. No. 3,835,110.

C. Direct synthesis of dimers

In stead of using S-protected cysteine as starting amino acid, use is made in this synthesis of N-protected amino acid cystine.

(1) (H—Cys—Tyr—Phe—Gln—Asn—Asp—OH)₂

One equivalent (Boc—Cys—OH)₂ is coupled to about two equivalents H-Tyr-Phe-Gln-Asn-Asp(OtBu)-OtBu with the aid of the HOBT/DCCI method of example A.2., resulting in the protected dimer:

(Boc—Cys—Tyr—Phe—Gln—Asn—Asp(OtBu)—OtBu)₂.

The Boc and OtBu protecting groups are now simultaneously removed by treatment with a mixture of trifluoro-acetic and anisole, under the conditions described in example A.2. Yield of (H—Cys—Tyr—Phe—Gln—Asn—Asp—OH)₂ is 68% on the basis of the protected cystine starting material.

Rf in Bu:Ac:Wa (3:1:1)=0.10 on SiO₂, melting point 230° C. (dec.).

(2) The following dimers are prepared in a way analogous to that given in C(1):

(a) (H—Cys—Tyr—Phe—Gln—Asn—Ala—OMe)₂ by coupling of (Boc—Cys—OH)₂ with H-Tyr-Phe-Gln-Asn-Ala-OMe, followed by cleavage of the Boc group with trifluoro-acetic acid.

(b) (H—Cys—Tyr—Phe—Gln—Asn—Ala—NH₂)₂ by coupling of (Boc—Cys—OH)₂ with H-Tyr-Phe-Gln-Asn-Ala-NH₂ followed by cleavage of the Boc group with trifluoroacetic acid.

EXAMPLE I

H-Cys(SO₃H)-Tyr-Phe-Gln-Asn-OH 5.0 g of the dimer obtained in B.1. is suspended in 50 ml water, after which 2 equivalents sodium sulphite and 1 equivalent sodium tetrathionate (Na₂S₄O₆) are added to the suspension at room temperature (25° C.). After stirring for 1 minute, a solution is obtained. This solution is put onto a basic ion exchange column (DEAE in acetate form), after which the column is eluted with 2% acetic acid solution until the eluate countains no more salts. The peptide is subsequently eluted from the column with a linear gradient of 0-20% acetic acid solution. The fractions containing exclusively the desired peptide, as monitored by thin layer chromatography, are collected and freeze-dried. Melting point 200° C. (dec.); Rf in Bu:Ac:Wa (3:1:1)=0.30 (SiO₂).

EXAMPLE II

The following peptides are prepared in a way corresponding to that described in Example I:
(a) H-Cys(SO₃H)-Tyr-Phe-Gln-Asn-Asp-OH; Rf=0.54
(b) H-Cys(SO₃H)-Tyr-Phe-Gln-Asn-Glu-OH; Rf=0.60
(c) H-Cys(SO₃H)-Tyr-Phe-Gln-Asn-Ser-OH; Rf=0.30
(d) H-Cys(SO₃H)-Tyr-Phe-Gln-Asn-Ala-OH; Rf=0.40
(e) H-Cys(SO₃H)-Tyr-Phe-Gln-Asn-Val-OH; Rf=0.43
(f) H-Cys(SO₃H)-Tyr-Phe-Gln-Asn-Ala-OMe; Rf=0.65
(g) H-Cys(SO₃H)-Tyr-Phe-Gln-Asn-Ala-NH₂; Rf=0.55
(h) H-Cys(SO₃H)-Tyr-Phe-Glu-Asp-OH; Rf=0.45
(j) H-Cys(SO₃H)-Tyr-Phe-Glu-Asn-OH; Rf=0.41
(k) H-Cys(SO₃H)-Tyr-Phe-Gln-Asp-OH; Rf=0.40
(l) H-Cys(SO₃H)-Tyr-Phe-Gln-Asn-OC₁₁H₂₃ Rf=0.55
The peptides (a) up to (e) have melting point above 240° C. The Rf values are measured in Bu:Ac:Wa (3:1:1) on SiO₂.

It is claimed as the invention:
1. Compounds of the formula:

$$\text{H—L-Cys—L-Tyr—L-Phe—L-Glu}(X_1)\text{—L-Asp}(X_2)\text{—B}$$
$$|$$
$$\text{SO}_3\text{H}$$

and their functional derivatives, wherein $X_1$ and $X_2$ represent hydroxy or amino and B represents:
(1) hydroxy or
(2) an amino-acid residue selected from the group consisting of L-Asp-OH, L-Asn-OH, L-Glu-OH, L-Gln-OH, L-Ser-OH, or HN-A-COOH, wherein A is an alkylidene group with one to about six carbon atoms.

2. A compound as recited in claim 1, wherein B represents L-Asp-OH.

3. A compound as recited in claim 1, wherein B is OH.

4. A compound as recited in claim 1, wherein B is L-Glu-OH.

5. A compound as recited in claim 1, wherein B is L-Ser-OH.

6. A compound as recited in claim 1, wherein B is L-Ala-OH.

7. A compound as recited in claim 1, wherein B is L-Val-OH.

8. A compound as recited in claim 1, wherein B is L-Asp-OH and both $X_1$ and $X_2$ are amino.

9. A compound as recited in claim 1, wherein B is hydroxy and both $X_1$ and $X_2$ are amino.

10. A pharmaceutical composition having psychopharmacological properties, comprising:
(A) a pharmaceutically effective amount of a compound of the formula:

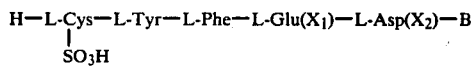

or a functional derivative thereof, wherein $X_1$ and $X_2$ represent hydroxy or amino and B represents:
(1) hydroxy or
(2) an amino acid residue selected from the group consisting of L-Asp-OH, L-Asn-OH, L-Glu-OH, L-Gln-OH, L-Ser-OH, or HN-A-COOH, wherein A is an alkylidene group with one to about six carbon atoms; and
(B) a pharmaceutically effective carrier therefor.

11. A composition as recited in claim 10, wherein B represents L-Asp-OH.

12. A composition as recited in claim 10, wherein B represents OH.

13. A composition as recited in claim 10, wherein B represents L-Glu-OH.

14. A composition as recited in claim 10, wherein B represents L-Ser-OH.

15. A composition as recited in claim 10, wherein B represents L-Ala-OH.

16. A composition as recited in claim 10, wherein B represents L-Val-OH.

17. A composition as recited in claim 10, wherein B represents L-Asp-OH and both $X_1$ and $X_2$ are amino.

18. A composition as recited in claim 10, wherein B represents hydroxy and both $X_1$ and $X_2$ are amino.

* * * * *